US012327262B1

(12) United States Patent
Benner et al.

(10) Patent No.: US 12,327,262 B1
(45) Date of Patent: *Jun. 10, 2025

(54) MEDICAL ACCOUNTABLE PROVIDER PLATFORM

(71) Applicant: RXANTE, INC., Portland, ME (US)

(72) Inventors: Joshua S. Benner, McLean, VA (US);
Aaron McKethan, McLean, VA (US);
Kimball Lewis, McLean, VA (US);
Daniel Smith, McLean, VA (US);
Morgan Beschle, McLean, VA (US);
Spencer Cherry, McLean, VA (US);
Loren Lidsky, McLean, VA (US)

(73) Assignee: RxANTE, INC., Portland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/503,505

(22) Filed: Nov. 7, 2023

Related U.S. Application Data

(63) Continuation of application No. 17/744,269, filed on May 13, 2022, now Pat. No. 11,842,365, which is a
(Continued)

(51) Int. Cl.
G06Q 30/0207 (2023.01)
G06Q 50/22 (2024.01)
(Continued)

(52) U.S. Cl.
CPC ......... G06Q 30/0207 (2013.01); G06Q 50/22 (2013.01); G16H 10/60 (2018.01);
(Continued)

(58) Field of Classification Search
CPC .... G06Q 30/0207; G06Q 50/22; G16H 10/60; G16H 20/10; G16H 40/20; G16H 40/63; G16H 50/20; G16H 50/30; G16H 50/50
(Continued)

(56) References Cited

U.S. PATENT DOCUMENTS 6,039,688 A * 3/2000 Douglas ............... A61B 5/4866
600/300
6,578,003 B1 * 6/2003 Camarda ............... G16H 20/10
705/2

(Continued)

FOREIGN PATENT DOCUMENTS

WO WO-2011062934 A1 * 5/2011 ......... G06F 19/3456

OTHER PUBLICATIONS

Heisler M, Hofer TP, Klamerus ML, et al. Study protocol: the Adherence and Intensification of Medications (AIM) study—a cluster randomized controlled effectiveness study. Trials. 2010;11:95. Published Oct. 12, 2010. doi:10.1186/1745-6215-11-95 (Year: 2010).*

(Continued)

*Primary Examiner* — Joy Chng
(74) *Attorney, Agent, or Firm* — Nixon & Vanderhye PC

(57) ABSTRACT

The technology described herein relates to using predictions about patients' future health care utilization and/or outcomes (e.g., patients' expected future adherence to medication regimens) and the expected economic benefits of targeted improvements in the same utilization and/or outcomes (e.g., reduced likelihood of hospitalization attributable to more consistent medication use) to implement more effective and efficient health care improvement programs. The technology described here computes which subset of patients should be included in a value-based health care provider payment scheme and what the specific bonus payment amounts should be such that expected benefits from better patient outcomes, once realized, are greater than the expected costs of the payment scheme itself.

20 Claims, 12 Drawing Sheets

Related U.S. Application Data continuation of application No. 16/163,734, filed on Oct. 18, 2018, now Pat. No. 11,334,902, which is a continuation of application No. 14/319,450, filed on Jun. 30, 2014, now Pat. No. 10,108,975.

(60) Provisional application No. 61/841,395, filed on Jun. 30, 2013.

(51) Int. Cl.
| | |
|---|---|
| *G16H 10/60* | (2018.01) |
| *G16H 20/10* | (2018.01) |
| *G16H 40/20* | (2018.01) |
| *G16H 40/63* | (2018.01) |
| *G16H 50/20* | (2018.01) |
| *G16H 50/30* | (2018.01) |
| *G16H 50/50* | (2018.01) |

(52) U.S. Cl.
CPC ............ *G16H 20/10* (2018.01); *G16H 40/20* (2018.01); *G16H 40/63* (2018.01); *G16H 50/20* (2018.01); *G16H 50/30* (2018.01); *G16H 50/50* (2018.01)

(58) Field of Classification Search
USPC ......................................................... 705/2–3
See application file for complete search history.

(56) References Cited

U.S. PATENT DOCUMENTS

| 8,666,926 | B1 | 3/2014 | Nease |
| 2008/0201174 | A1* | 8/2008 | Ramasubramanian ..................... G16H 20/10 705/3 |
| 2010/0205008 | A1 | 8/2010 | Hua |
| 2012/0179002 | A1 | 7/2012 | Brunetti |
| 2012/0310661 | A1 | 12/2012 | Greene |
| 2013/0073306 | A1* | 3/2013 | Shlain ................... G06Q 10/06 705/2 |
| 2013/0096953 | A1 | 4/2013 | Beverly et al. |
| 2013/0311205 | A1 | 11/2013 | Creswell et al. |
| 2013/0317839 | A1 | 11/2013 | Creswell et al. |

OTHER PUBLICATIONS

Linn AJ, Vervloet M, van Dijk L, Smit EG, Van Weert JC. Effects of eHealth interventions on medication adherence: a systematic review of the literature. J Med Internet Res. 2011;13(4):e103. Published Dec. 5, 2011. doi:10.2196/jmir.1738 (Year: 2011).*
Heisler M, Hofer TP, Klamerus ML, et al. Study protocol; the Adherence and Intensification of Medications (AIM) study—a cluster randomized controlled effectiveness study. Published Oct. 12, 2010. Trials. 2010;11:95. Doi: 10.1186/1745-6215-11-95 (Year: 2010).
Linn AJ, Vervloet M, van Dijk L, Smit EG, Van Weert JC. Effects of eHealth interventions on medication adherence: a systematic review of the literature. Published Dec. 5, 2011. J Med Internet Res. 2011;13(4): e 103. Doi: 10.2196/jmir.1738 (Year: 2011).

* cited by examiner

PRID — John Smith Medical Group (300000004) ▼

Home | Patients | Practice | Resources | Management

Welcome, User
Settings | Logout

Welcome

Some of our patients are at risk of poor drug therapy outcomes. We'll show you who they are and how you can earn big bonuses by keeping them on track.

3 simple steps to earn bonuses this quarter:

① Determine if patient understands purpose of medication, address concerns, and remind patient to take medications.
② Manage patient to 10 or fewer untreated days per quarter.
③ Address any prescribing opportunities that arise.

Tips:

▶ Watch this 1 minute video to learn about the new "Contact Soon" feature.

Progress this quarter — BPR
$2,750 remaining
$750 missed — BPM 53 patients still need your attention — PNA Sign Agreement    View Patient List Help | Terms & Conditions

| | | | |
|---|---|---|---|
| Home | Patients | Practice | Resources | Management |

John Smith Medical Group (30000004) ▼

← Back to patient list

Jane Armstrong  Mailing Address
Birthdate: 07-10-1938   1 Happy St.
Phone: (123)555-7417   Chicago, IL 60611

| Assess patient | Patient Info | Add notes | Key facts |

Last year: 5 medications in 5 therapy classes — KF1

Last year: 2 prescribers, 2 pharmacies — KF2

Patient Medication Adherence*

| | BLOOD PRESSURE |
|---|---|
| | 5 days missed |
| MEDICATION | Moexipril-Hydrochlorothiazide 90 Day Supply |
| BONUS REMAINING | $50 |
| REFILL DUE DATE | 2014-04-24 |
| PRESCRIBER | Dr. H. Smith |

*Reporting Q2 for 2014, based on claims data through Apr 8th, 2014

Welcome, User
Settings | Logout

FIG. 9

Home | Patients | Resources | Management     Welcome, User Settings | Logout

Agreement | Providers | Practice

Metrics

PRID: John Smith Medical Group (30000004) ▼

Summary for Q2 of 2014* — PRS

| Therapy | Number of patients | Average Untreated Days |
|---|---|---|
| Diabetes | 19 | 6.47 |
| Hypertension | 25 | 5.00 |
| Cholesterol | 26 | 7.42 |
| Diabetes Treatment | 8 | |
| All Therapies | 53 | 6.30 |

Adherence bonus for 2014* — PRBS

■ Missed    □ Remaining

Q2 (In progress)    Q3    Q4    Q2

Performance for all therapies
- $750 / $2,750    Total: $3,500
- $750 / $2,750    Total: $3,500

Diabetes bonuses
- $300
- $300

FIG. 10

| Home | Patients | Practice | Resources | | Welcome, User Settings \| Logout |
|---|---|---|---|---|---|
| Practice Mgmt | User Mgmt | | Reports | Management | |

| Overview | | | | | | | | | |
|---|---|---|---|---|---|---|---|---|---|

Welcome

3 simple steps to onboarding your practices in this year's bonus program:
1. Review your practices on the practice management page and update practice contact information where necessary.
2. Onboard your practices by teaching them about the program and collecting the names and email addresses of their designated users who will be using the System.
3. Enter the information for these designated users on the user management page. An automatic email will be sent to each designated user containing a link that will allow them to register.

If you have any questions we are just an email away: john@email.com

Top 4 Non-Participating Practices PRNAME — ES — PRREGION — PRBEP

| TIN | Practice NPI | Practice Name | Engagement Score* | Region | Bonus-Eligible Patients | Participated in 2013 | Participating in 2014 | Signed COP in 2014 | Primary Liaison | Actions |
|---|---|---|---|---|---|---|---|---|---|---|
| 30000005 | | Mike Johnson Medicine Associates | ★★★★ | West | 150 | No | No | No | | Details |
| 30000002 | | Andrew Johnson Medicine Associates | ★★★ | North | 137 | No | No | No | | Details |
| 30000001 | | Jane Smith Family Practice | ★ | Central | 115 | No | No | No | | Details |
| 30000004 | | John Smith Medical Group | N/A | East | 53 | No | No | No | | Details |

PRID

*Engagement Score: N/A=Engagement not Applicable ★=Not Engaged ★★=Somewhat Engaged ★★★=Engaged ★★★★=Highly Engaged Help \| Terms & Conditions

FIG. 11

MEDICAL ACCOUNTABLE PROVIDER PLATFORM

CROSS-REFERENCES TO RELATED APPLICATIONS

This application is a continuation of U.S. patent application Ser. No. 17/744,269 filed May 13, 2022, which is a continuation of U.S. patent application Ser. No. 16/163,734 filed Oct. 18, 2018, (now U.S. Pat. No. 11,334,902) issued on May 17, 2022, which is a continuation of U.S. patent application Ser. No. 14/319,450 filed Jun. 30, 2014 (now U.S. Pat. No. 10,108,975) which claims priority to U.S. Patent Application No. 61/841,395, filed Jun. 30, 2013, the entire contents of which are incorporated herein by reference.

BACKGROUND AND SUMMARY

Financial incentive programs have been available in the medical profession for quite some time. For example, pay-for-performance programs are incentive-based programs that reward members in the health care community (e.g., doctors, hospitals, pharmacies) for meeting pre-established targets for delivery of healthcare services. These targets for delivery of healthcare services could cover a variety of fields in the healthcare industry including, but not limited to, adherence to one or more medication regimens, reduction of hospital readmissions, and/or timely participation in medical detection processes (e.g., receiving a mammogram when the patient is of a certain age).

In fact, there are many examples in health care of financial incentives (or negative incentives/penalties) offered by health insurers, pharmacies, pharmacy benefit managers, health care delivery systems, or pharmacy chains to health care professionals in exchange for performing particular services at defined levels. For example, a bonus can be achieved when a health care provider ensures that a certain percentage of the eligible patient population adheres to a drug therapy (e.g., blood pressure medication) according to clinical guidelines. Incentives can also be achieved based on defined performance quality measures. For example, a bonus can be achieved when a health care provider ensures that average blood sugar levels among eligible patients do not surpass certain levels.

Bonus payments are typically calculated as a function of an available bonus pool (e.g., an amount of money) divided by the number of expected or potential bonus payouts. In other cases, the magnitude of bonus payments may, for example, be simply benchmarked to industry norms or set as an amount that is believed to be conducive to induce provider engagement and participation.

However, there are certain drawbacks to these programs. For example, these incentive programs are generally applicable to a large population of patients where the rewards are distributed to healthcare professionals on behalf of the measured performance of patients across the population. That is, the bonus pool is allocated evenly for each individual in the population thus making the incentive associated with each individual relatively small when the population is large.

A fundamental shortcoming in the art is a lack of technology or set of analytic processes that systematically calculates and offers a financial bonus payment to a health care professional that is determined by the factors mentioned above, as well as the predicted risk profiles of patients eligible for inclusion in quality measures and the expected financial or economic benefits that could accrue if patients achieve performance goals as intended by the bonus payment scheme itself (e.g., if population-level increases in medication adherence are achieved as intended by the bonus available to relevant health care professionals, the average expected cost of those patients will fall by a specific, predictable amount). Another shortcoming in the art is that there is no technology that is directed to prediction-driven or prediction-derived outcomes payments to health care professionals designed to return the increased (or even maximized) economic gains while reducing (or even minimizing) program and bonus payment costs. Thus, there is a need for a system that improves upon these drawbacks and provides for solutions mentioned above.

The technology described herein relates to using predictions about patients' future health care outcomes (e.g., patients' expected future adherence to medication regimens) and the expected economic benefits of targeted improvements on certain performance measures (e.g., reduced likelihood of hospitalization attributable to more consistent medication use). Certain technology related to predicting patients future health care outcomes is described in commonly assigned U.S. patent application Ser. No. 13/729,817, the entire contents of which are incorporated herein by reference. These factors help compute which subset of patients should be included in a payment scheme and what the specific bonus payment amounts should be such that expected benefits from better patient outcomes, once realized, outweigh the expected costs of the payment scheme itself. While the description herein is made with respect to a medication adherence example, it will be understood that the description in this regard is illustrative and non-limiting. The technology described herein may be applicable to any of a wide range of conditions and incentive programs.

BRIEF DESCRIPTION OF THE DRAWINGS

FIG. 6 shows a non-limiting example user interface of the system;

FIG. 7 shows a non-limiting example user interface showing patient listings in the customer provider incentive system;

FIG. 9 shows a non-limiting example user interface providing further patient details;

FIG. 10 shows a non-limiting example user interface providing summary information;

FIG. 11 shows a non-limiting example user interface providing further summary information.

DETAILED DESCRIPTION OF THE TECHNOLOGY

Figure 1:
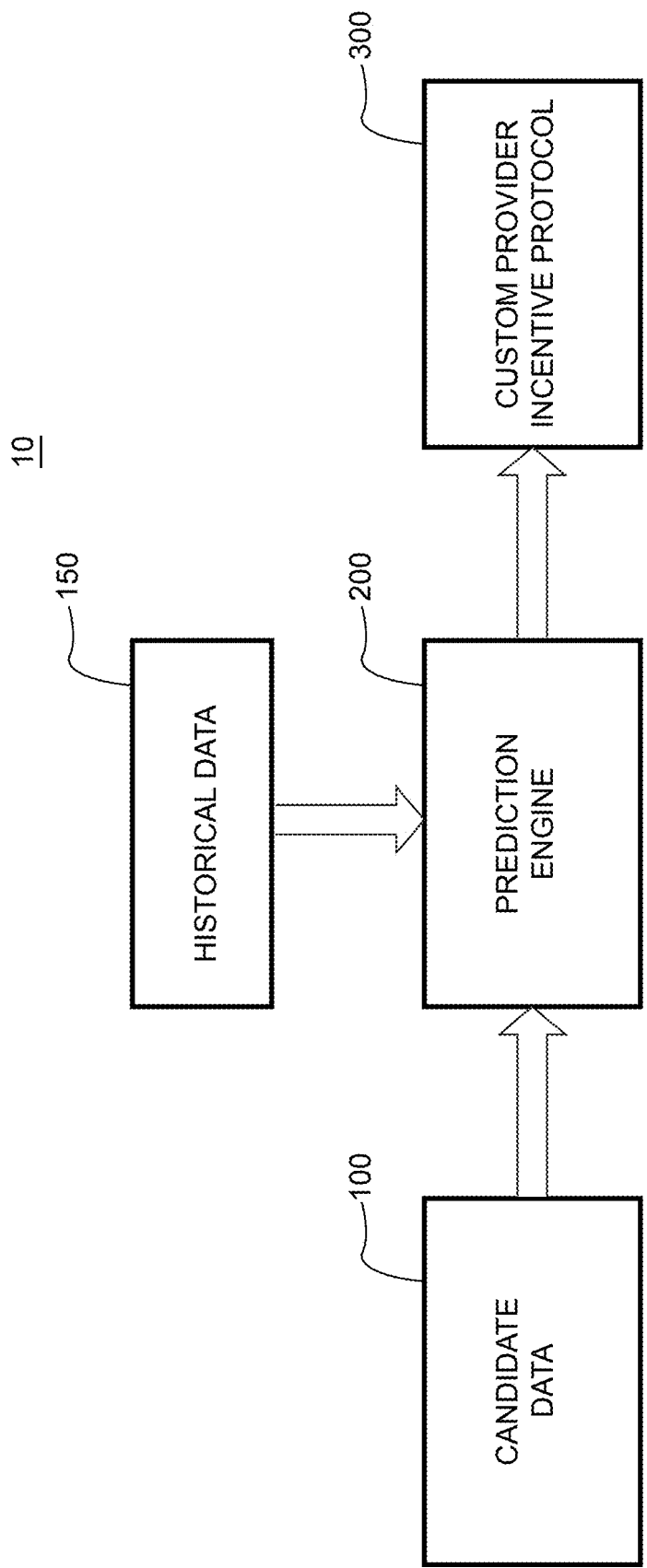
FIG. 1 is an illustrative block diagram of a system for a custom provider incentive protocol.

Most health services are paid for on a fixed fee basis (i.e., "fee for service"), but various forms of performance or value-based payment have been adopted in recent years. For example, certain health care payment models typically make uniform bonus payments available to health care professionals in exchange for performing certain tasks, ensuring certain processes, or contributing to certain outcomes. However, these models have several deficiencies. As an example, bonus payment programs and related performance measures tend to require that services are rendered, or targeted performance improvements are attained across large numbers of patients who meet certain criteria (e.g., all patients diagnosed with a particular condition). Consequently, available bonus dollars for these programs are distributed over relatively large populations and, hence, incremental bonus dollars available per patient tend to be very small. This is disadvantageous because it reduces the incentive for practices to engage in the bonus payment programs due to the large number of patients the practice will be required to monitor or engage in order to obtain the bonus and incentivize the practice to participate in the program.

With very large populations of patients included in such programs, doctors, pharmacists and other health care professionals are faced with very large numbers of patients whose care must be better managed in order to earn the available potential bonus payments. The potential to incur substantial cost and expend resources, and related logistical challenges in providing extra support to large numbers of patients with disproportionately low incentive payment may often result in health care professionals being less likely to participate in bonus payment programs, rendering them ineffective.

Moreover, since such potential bonus payments can be relatively small (especially where relatively large numbers of patients are included), health care professionals often conclude that the benefits of participating or undertaking extra efforts to achieve the performance goals of a payment scheme overshadow the potential to earn small potential bonus payments. Thus, payment schemes designed to induce changes in the behavior of health care professionals have often returned disappointing results.

Furthermore, bonuses can also often be earned by providers when patients are healthier-even if the provider played little or no role in achieving the healthy outcome. Thus, what is needed is a system that increases the efficiency of these programs in a way to find a patient population that can (a) exclude patients from bonus programs who appear highly likely to achieve the program's goals without additional intervention and (b) exclude patients that are highly unlikely to achieve the program goals even with additional intervention.

The technology described herein improves upon such disadvantages and is directed to deriving and using predictions about patients' future health care outcomes (e.g., patients' expected future adherence to medication regimens) and the expected economic benefits of targeted improvements on certain performance measures. The system uses predictions about patients' future health care outcomes (e.g., patients' expected future adherence to medication regimens) and the expected economic benefits of targeted improvements on certain performance measures (e.g., reduced likelihood of hospitalization attributable to more consistent medication use) to determine which subset of patients should be included in the payment scheme and what the specific bonus payment amounts should be such that expected benefits from better patient outcomes, once realized, outweigh the expected costs of the payment scheme itself. That is, the technology is capable of narrowing the population of patients to a subset of (a) patients that are unlikely to achieve a desired health outcome without intervention and (b) patients who, if achieve the desired health outcome, would aid in maximizing the benefit of the incentive program. Additionally, the technology is also capable of attributing certain patients to one or more practitioners and thus identifying practitioners that are beneficial to a particular incentive program (e.g., aid in maximizing the benefit of the incentive program).

The system provides timely, clinically actionable information to health care professionals that can enrich and inform provider/patient interactions in accordance with patients' risk profiles derived from predictive algorithms. The system also facilitates, computes, and manages prediction-derived, financial incentives for providers to help their patients improve medication adherence.

The system combines patient-level predictive algorithms regarding, for example, medication adherence and other quality-related outcomes, data on other patient characteristics derived from available data sources, and exogenously determined financial and other capacity or workflow constraints or inputs from the end user (client). The result is an iterative system of prediction, patient risk assessment, intervention decision support, and learning that achieves efficient population-level improvement in, for example, adherence and other medication quality measures.

Included in the system are certain core elements. First, predictive analytics is used to identify a preferably optimal subset of a larger patient population whose cumulative future predicted modifiable health care outcomes create the improved, and preferably, largest possible economic gains to the sponsor of the bonus program. Analytics are used to compute the magnitude of incremental bonus payments optimizing cost reduction goals of the sponsor of the bonus program and increased economic gains attributable to improved targeted health outcome improvements by the selected patients. The system can also employ identification and visual display, for example, via a web-based portal available to health care professionals eligible for bonus payments, of patient-specific information regarding the risk profiles of selected patients, the potential causes of their sub-optimal performance on selected medication quality measures, including, for example, adherence, and suggested action steps to achieve targeted improvements in selected performance indicators. Of course, the system is not limited to providing this information using a visual display and can generate the desired information and convey/transmit the information to a client and/or third party (e.g., for display by the client/third party). This information could be transmitted using, for example, an electronic medical record.

The technology establishes the basis for prediction-driven performance improvement programs in health care that have the potential to improve the prevalence and performance of health care financial bonus programs for health care professionals designed to achieve targeted improvements in health care outcomes. For example, in the case of prescription medication adherence, the system further includes medication adherence commensurate with the value that those targeted improvements create to sponsors of such programs.

FIG. 1 is an illustrative block diagram showing elements of an example embodiment. The basic elements 10 are described very generally with respect to FIG. 1 and will be described in further detail below with respect to the remaining drawings. The system includes, for example, candidate patient data 100, which is processed as described herein and provided to a prediction engine 200. The prediction engine 200 is developed as described below and includes development of a prediction function which is based, at least in part, on an analysis of historical patient data 150 which may include historical data on, for example, intervention performance (for example, and without limitation, tracking data). When the prediction function of the prediction engine 200 is applied to the candidate patient data 100, a tailored patient-specific score is output and can be provided to a custom provider incentive protocol 300. As described further below, the custom provider incentive protocol 300 can provide patient-specific tailored medical incentives for health care providers.

Figure 2:
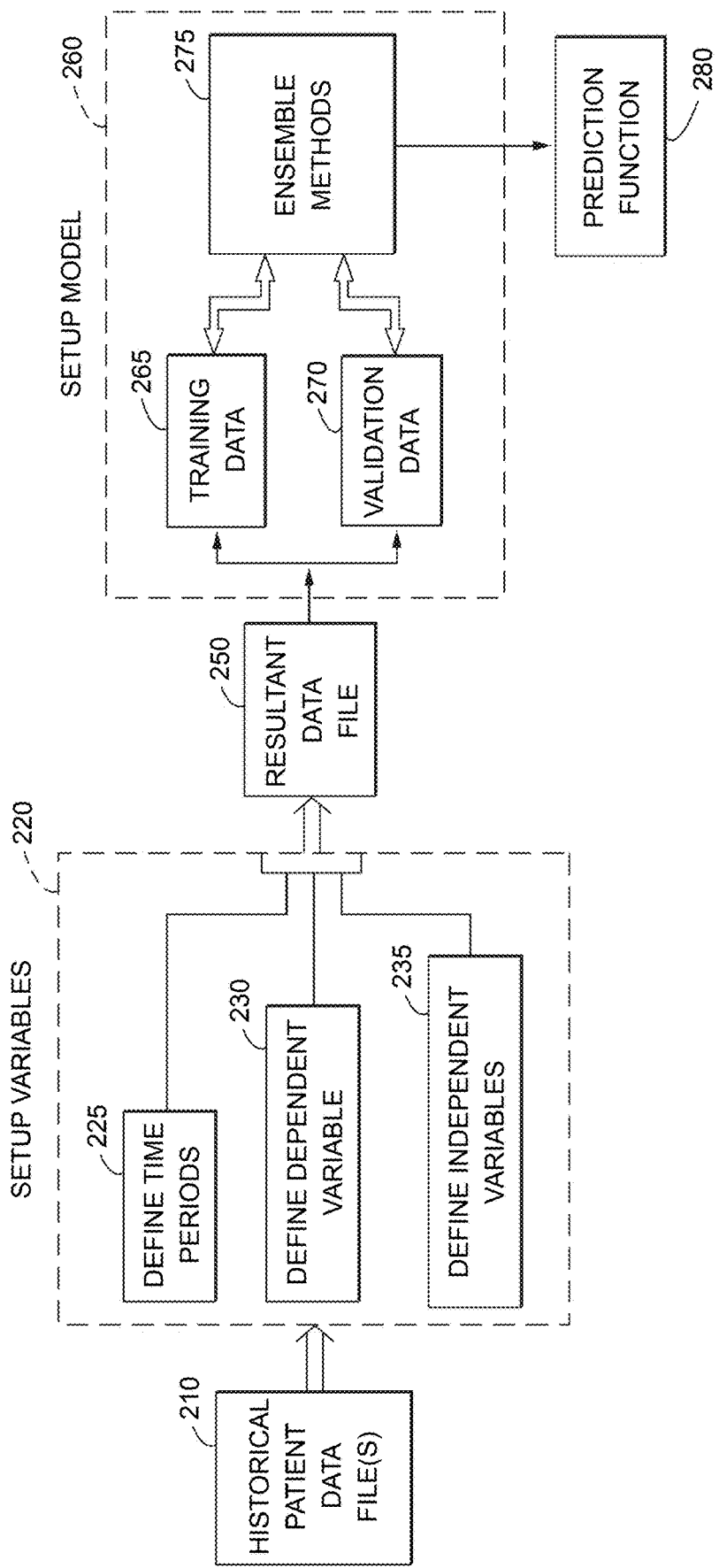
FIG. 2 is an illustrative block diagram of an example setup procedure used to define a prediction function in accordance with an example embodiment.

FIG. 2 shows an illustrative block diagram of an example setup procedure used to define a prediction function in accordance with an example embodiment. As illustrated in FIG. 2, historical patient data 210, which may be in the form of a retrospective data file (or multiple files) from the implementation entity or program sponsor, is provided. Data in these files may include, for example, demographic, survey, clinical and/or administrative claims data about patients who would have been candidates for the adherence program, plus filled prescriptions data to allow for calculation of actual adherence after initiation of the medication therapy of interest. It will be understood that the data sources may vary and may include other example data, such as, for example, administrative claims, electronic medical records, lab results, patient surveys, sociodemographic detail, consumer purchasing data, etc. It will also be understood that different and multiple sources of data may be used to determine any number of independent variables for use in developing the predictive function described below.

The historical patient data 210 is analyzed and used during setup 220 to define certain variables 225, 230 and 235, for example, which may be used to determine a prediction function 280. For example, certain time periods 225 may be defined to assist in the extraction of various variables. Time periods of interest 225 may include, for example, an inception window or range of dates between filled prescriptions for the target medication which may be used to identify candidate patients for the adherence program. An index date for each patient which reflects the date of the first filled prescription for the target medication during the inception window may also be defined. It may also be useful to define a look-back period during which the pre-index information is collected about each patient. A common example look-back period is one year, but it will be understood that the look-back period can range from zero days to many years. In addition, a follow-up period may be defined. A common follow-up period may typically be one year, but the follow-up period may range from one day to many years.

It is next preferable to define a dependent variable 230, sometimes also referred to as the measure to be predicted. In the medication adherence example, a common measure of medication adherence is the binary outcome of a proportion of days covered being greater than or equal to eighty percent. In other words, this dependent variable 230 would be satisfied if the patient obtained sufficient prescriptions to have the medication on hand for at least eighty percent of the days in the follow-up period. It will be understood that definitions of adherence may vary and that the definition set forth above is made by way of illustrative non-limiting example. Other examples may include, proportion of days covered, medication possession ratio, discontinuation, etc. Additionally, threshold values may likewise vary, e.g., >=80%; >=70%; >=60%, etc. With the dependent variable 230 defined, it may then be useful to define a number of independent variables 235. It should also be appreciated that the proportion of days covered could be a dependent variable itself (e.g., instead of proportion of days covered being a binary calculation when compared against a threshold).

Independent variables 235, may be developed based on published studies of factors associated with adherence in a particular therapy area. These may, for example, fall into three broad category areas. One broad category area may be, for example, attributes of the patient, e.g., age, sex, county of residence, health status and prior health care utilization. Another broad category may include, for example, attributes of the target drug regimen, e.g., specific drug, strength, quantity dispensed, cost, etc. A third broad category may include, for example, attributes of the health care system, e.g., prescriber's specialty, number of pharmacies used, health plan design, etc.

Independent variables 235 may include variables known to be predictive of adherence and may include variables not known to be associated with adherence, but which can be rapidly tested using data mining methods to derive these from the patient data itself. For example, software running on the computer system 500 may be used to automatically create independent variables. Other independent variables may include complex interactions between various predictors. These variables generally may relate to the presence/absence and frequency of all possible drugs, diagnoses and procedures in the patient look-back period. Survey data may also be included in the provided data and all possible responses may also be included. It will be understood that different and multiple sources of data may be used to determine any number of independent variables for use in developing the predictive function.

A resultant data file 250 is generated to include the setup variables 220 that are generated as described above. Patient data files may be augmented and restructured to provide a common data structure for the resultant data file 250 in order to more efficiently process the data contained in the resultant data file 250. The resultant data file includes information for each patient of interest from the historical patient data files 210 and include the setup variables 220 discussed above.

Once the resultant data file 250 is created, it is provided to a further model setup procedure 260, that will result in a prediction function 280 that is then applied to candidate data to produce a patient-specific score, in this case an adherence score. Creation of the prediction function 280 is discussed in more detail herein.

In general, the resultant data file is analyzed using multiple statistical methods to develop the best predictive function when tested and validated against the historical patient data in view of the fact that actual adherence can be determined with respect to the historical patient data. As a specific example, the resultant data file 250 may be divided into two parts: a "training" data file 265 and a "validation" data file 270. The system may then use, for example, multiple statistical methods 275, including, for example, any one or more of the following: logistic regression, random forests, classification and regression trees (CART), stacking, boosting, or the like, on the training data 265. These statistical methods may generally be combined, and as such, be referred to as ensemble methods 275 for determining or creating a model or predictive function based on the training data 265 that will yield highly predictive results. For example, as noted above, the resultant data file 250 may be partitioned into two parts, the "training" data 265 and the "validation" data 270 as described above. For the purposes of example, the resultant data may be randomly partitioned so that eighty percent (80%) are the "training" data 265 and the remaining twenty percent (20%) of the resultant data are in the "validation" data 270 set. It will be understood that any statistically proper partitioning may be selected based on the type of analysis and regression to be applied to the data. The models or predictive functions are developed and tested using the training data 265 over multiple statistical methods as discussed above (e.g., ensemble methods), and then testing the predictive function against the validation data 270, which is also commonly referred to as held-out data. A predictive function that is derived from the training data 265 may then be applied to the validation data 270, and the predictive function that is determined to perform best on the validation data 270 is selected as the predictive function to be applied to the candidate patient data as described below. It will be understood that any number of other possible statistical methods may be used to generate the resulting prediction function, and that the system and method disclosed is not limited to the particular example statistical methods described herein.

In this manner, the independent variables or predictors are used to predict the dependent variable using the predictive function 280 created on the basis of the historical patient data 210. The predictive function 280 is used in creating a patient-specific score representative, as a non-limiting example, of a patient's probability of being adherent. For example, the patient-specific score could be an integer value between 0 and 100 representing a percent chance of a patient being adherent (e.g., 0.74 represents a 74% chance the patient will be adherent). This score takes into account the medical history of each patient, as discussed above, as well as the other setup variables used to determine the probability of a patient's adherence. Thus, each patient in a particular practice will have a patient-specific adherence score generated using the above-mentioned factors and this score will be used, in part, to create a subset of patients in the practice that will have the highest likelihood of helping a health care provider (e.g., health insurance company) achieve its performance goals.

Figure 3:
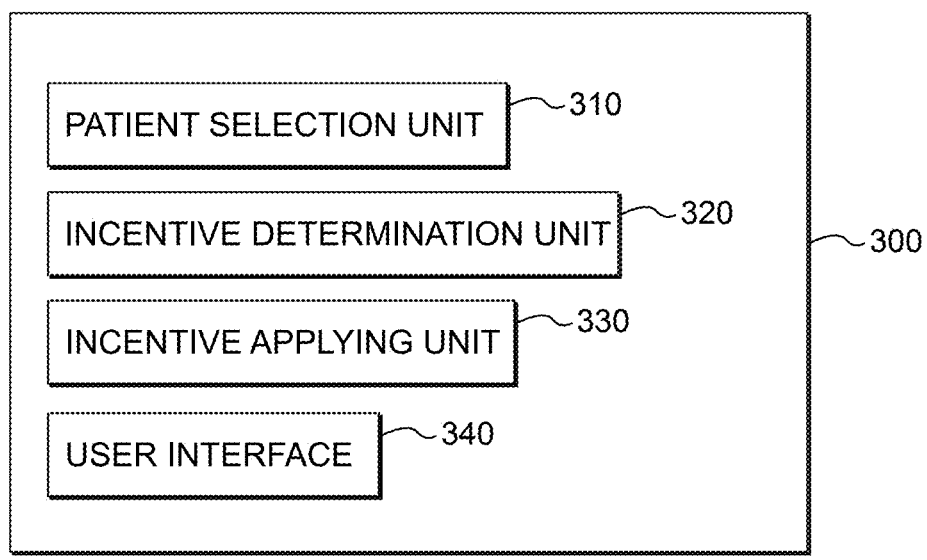
FIG. 3 is an illustrative block diagram of a custom provider incentive protocol.

FIG. 3 is an illustrative block diagram of a custom provider incentive protocol 300. The custom provider incentive protocol 300 can receive data from the prediction engine 200 so that a custom tailored incentive plan can be provided for a health care provider. This data could include, for example, the patient-specific scores representing, for example, the probability of each patient's adherence to a drug regimen and/or medical services. The customer provider incentive protocol 300 can have a patient selection unit 310, an incentive determination unit 320, an incentive applying unit 330, and/or a user interface 340.

Certain medical and health organizations (e.g., medical insurance companies) can be held to various government mandated standards. The standards can impose both bonuses and penalties for meeting (or not meeting) the criteria set out in the standard. As a working example, a government agency could require a health care provider, such as a medical insurance company, to ensure that 75% of their enrolled patients are timely taking their blood pressure medication within a given time period (e.g., 1 year). If the health care provider meets the mandated requirements (e.g., 75% of patients timely taking blood pressure medication), the government could issue a bonus incentive to the provider. Likewise, the government could institute a penalty on the provider (e.g., a negative incentive) if they do not meet the requirements.

The health care provider would then work with the medical practices (e.g., doctors and hospitals) to make sure that the patient population meets the particular standard. As explained above, motivating practices with larger patient populations to participate in such programs is difficult because bonus payments are typically uniformly spread across the population of patients. Furthermore, the larger the number of patients eligible to participate in this program, the more unlikely a practice will be able to manage their adherence. Thus, the protocol 300 can take into account the requirements set by the standard for the health care provider in order to narrow the patient population giving the provider and/or practice the highest probability of achieving the goal.

In more detail, the patient selection unit 310 may select a group of patients eligible for a particular incentive. For example, a government agency could mandate that an insurance company require 75% of its patients eligible for blood pressure medication to be adherent to their drug regimen. If the company already has 71% of its patients being adherent, the patient selection unit 310 could select a group of patients to achieve the remaining 4% (or more). For example, the patient selection unit 310 may retrieve a list of the patient-specific scores, as discussed above, for each patient in a particular practice that is taking blood pressure medication. The patient-specific score would be reflective of the probability that the patient will adhere to his/her prescription within a given time frame. Thus, the patient selection unit 310 can determine the subset of patients that give the company/practice the highest chance of achieving at least the missing 4% in the goal.

The unit 310 can accomplish this, for example, and without limitation, by identifying a group of patients that are not necessarily fully adherent to their blood pressure regimen, yet have a higher probability than other patients of being adherent with some management from the practice. That is, the list of patients would be within a range of scores maximizing expected outcome, reflective of not being 100% adherent, yet having a higher probability of being adherent with some tailored assistance or intervention from a participating practice. For example, a practice may have a large number of patients that are completely adherent as well as a number of patients that are entirely non-adherent. The patient selection unit 310 will help identify the patients in the "middle ground" that are not entirely adherent, yet, based on their patient-specific score have a higher likelihood of being adherent (e.g., with some help from the practice). Once this subset is determined, the protocol 300 can tailor the bonus incentives for the narrowed group of patients in order to provide larger incentives to the practice for each individual patient.

More specifically, the incentive determination unit 320 can provide data relating to both the type of incentive (e.g., patients eligible for blood pressure medication) as well as the total amount of financial incentive allocated for the program (e.g., $5,000 for all patients). For example, if a bonus incentive for a given quarter is $5,000 for 75% of the patients adhering to their blood pressure regimen, and a practice has 5,000 eligible patients, the incentive would normally be spread across each patient (i.e., $1 per patient that is adherent). However, it can be extremely difficult for a practice to monitor 5,000 patients to ensure that they are all adherent to their blood pressure medication. The patient selection unit 310 would thus "filter" the patients that would be highly adherent (as those patients would not need managing) as well as the patients that have little to no likelihood of being adherent (i.e., patients that would not be adherent even if the practice managed them). The selection of patients would result in a subset that is not entirely adherent but having a greater (e.g., highest) likelihood of being adherent with management from the practice.

The incentive determination unit 320 may then apply customized incentives for each patient. For example, if in trying to find the "4%" of patients to make up the required 75%, the unit 310 may select a group of 100 patients that are not entirely adherent but have a high probability of being adherent with enhanced management from the practice. The incentive determination unit 320 could then determine that each patient that is selected will have a bonus amount of $50 for being adherent during a given time frame. Thus, the incentive determination unit 320 advantageously applies a higher incentive to each patient in the subset making it more likely that the practice will engage the patient to ensure that the patient is adherent to their blood pressure regimen. Of course, the incentive determination unit does not necessarily have to apply the bonus amount equally to the subset and can give greater/lesser bonus amounts to each patient based upon certain criteria. The incentive determination unit 320 can also apply other factors as well including time limit durations for when the incentive is active (e.g., over a span of 3 months) as well as a threshold percentage/number of patients that must participate to receive the incentive. Again, conventional incentive programs normally distribute the incentive equally on a per-patient basis among the eligible patients. However, using the patient-specific score, the incentives can be custom tailored so that higher incentives are associated with certain patients based on their score. It should also be appreciated that the incentive could also be constructed so that a practice can be provided with a panel of patients to manage and the incentive is paid only if the rate of adherence across the specifically selected panel exceeds a threshold value (e.g., to allow for an even higher incentive amount for the provider).

The incentive applying unit 330 then applies the incentive for each patient so that the practice will know how much incentive amount (e.g., money) can be achieved by having the patient be adherent. Thus, the protocol 300 can narrow the list of patients so that the narrowed list will result in a much more manageable number for a practice to engage in achieving adherence while providing significantly greater bonus incentives for each patient that is adherent. This allows the practitioners (e.g., doctors) to take advantage of the bonus payment program by treating fewer high risk/need patients to satisfy the minimum patient criteria while achieving the maximum bonus amount. This effectively gives both the health care provider as well as the practice the highest likelihood of achieving the goals mandated by the government program.

The incentives for each patient could be presented to a user via a user interface 340. For example, the user interface 340 may preferably be a web-based interface accessible by health care provider staff where a list of the subset of patients most eligible for a particular incentive could be provided, as well as access to each patient's relevant medical history. An example user interface is shown in FIGS. 6-12, described in further detail below. It should be appreciated that the data may not necessary need to be conveyed using a visual display (e.g., a user interface) and could be compiled into a transferable record (e.g., an electronic medical record) that could be provided/transmitted to a client and/or third party. By providing custom tailored incentives for each patient using the patient-specific score, the health care provider would have incentive to participate in the incentive program thereby also providing a greater degree of wellness for the patient.

Figure 4:
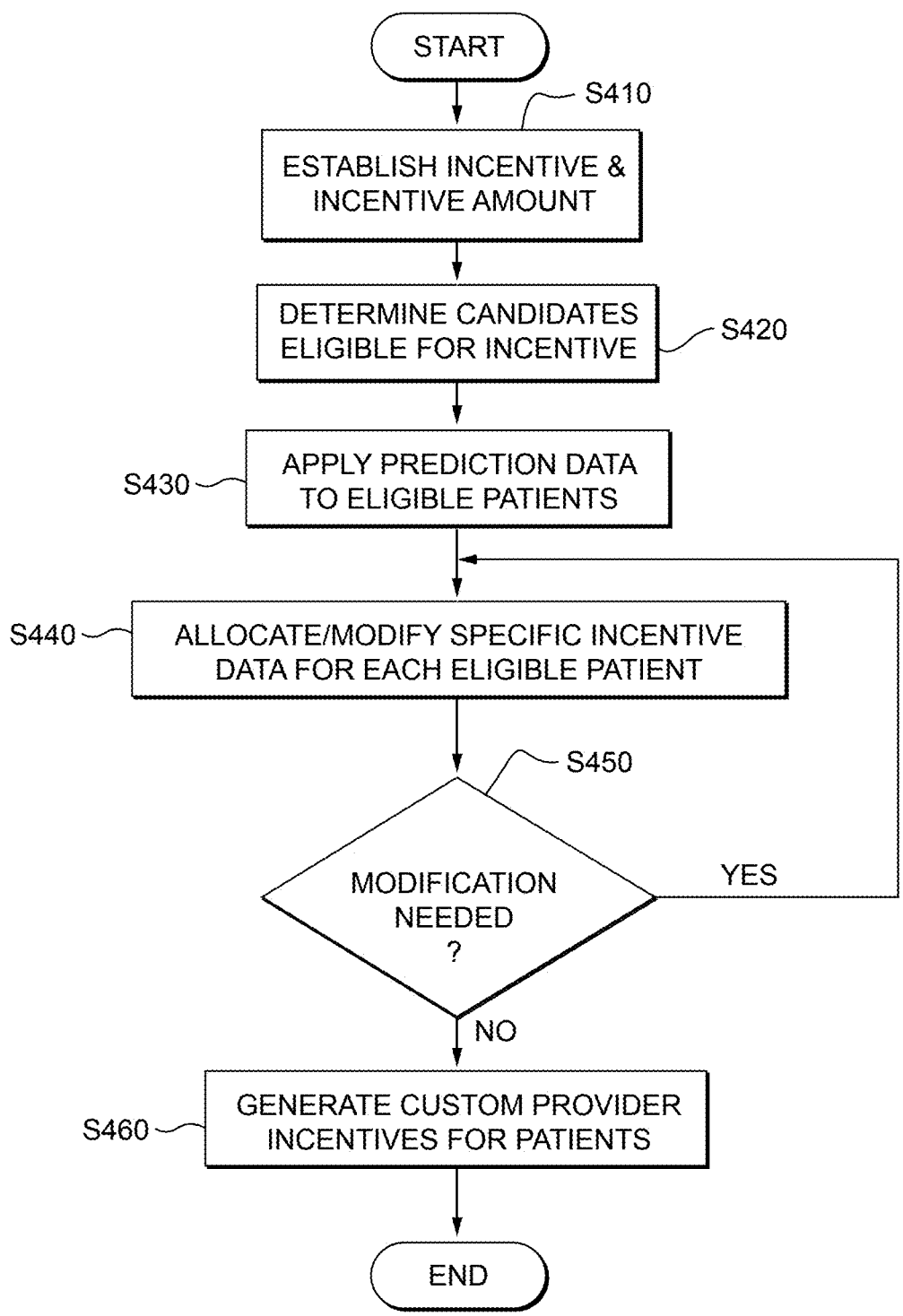
FIG. 4 is an illustrative flowchart for deriving a custom provider incentive protocol.

FIG. 4 is an illustrative flowchart for deriving a custom provider incentive protocol. The flowchart illustrates a non-limiting example of processes carried out by the system 10, and more specifically the protocol 300.

The protocol 300 may first establish the boundaries of the incentive including the overall amount for the incentive and the rules for being eligible for the incentive (S410). Using the example above, if a health care provider is required to have 75% of its patients adherent to blood pressure medication, and the provider currently has 71% of patients being adherent, the protocol 300 can take into account the required additional 4% needed to achieve the 75% goal in applying the incentive. Thus, the protocol 300 would apply an overall amount for an incentive (e.g., $5,000) over a smaller targeted population of patients in a given practice. Of course, certain other factors may be applied for determining the details of the incentive and are in no way limited to a financial dollar amount and/or a generic class of patients.

Upon determining the incentive details, the protocol 300 may determine the candidate patients eligible/targeted for the incentive (S420). Using the example above, the protocol 300 can determine which patients are eligible (or currently being prescribed) for blood pressure medication. Of course, other factors may apply that would potentially broaden or narrow the list.

Once the list of eligible patients is determined, the protocol 300 may apply the patient-specific score to eligible patients thereby altering the incentive amount for each patient (S430). Using the example above, the protocol 300 can find the patients having a score within a range that is not entirely adherent yet having a higher likelihood of adherence (e.g., with help from management of the practice). Thus, instead of having a list of 5,000 patients that are currently taking, or are eligible for, blood pressure medication, the list could be reduced to, for example, 100 patients that will help the company and practice achieve the remaining "4%." Thus, health care providers could effectively narrow the list of patients that may need these services thus encouraging the provider and practice to participate in the program.

The protocol 300 can optionally alter the incentive amount tailored for each patient based on their patient-specific score by allowing a user to provide additional variables that could effectively alter the score and alter the incentive amount (S440). If further modification is required (S450) (e.g., based on various user input), the system can modify/update the incentives for the patients (S440). If no further modification is necessary, the system can generate a list (or subset of the list) of patients together with associated incentives (S460). As a non-limiting example, the list could be ordered by the patients having the highest associated financial incentive amount. The list could also be truncated to only show a subset of patients with at least a particular incentive amount (e.g., $500 or more). This list of patients could be displayed using the user interface 340, as discussed above and described in greater detail below.

By providing this information to the health care provider, the provider can focus their efforts and encourage the patient to follow a particular medical treatment protocol (or in some instances not seek any medical treatment) while discouraging the provider from encouraging patients that may not be of immediate need of these services/drug regimens. The custom tailored incentives would also more likely encourage a health care provider to participate in the incentive program as the list would most likely produce a smaller subset of individuals required to need the particular medical therapy while providing a significantly higher financial incentive per patient.

Figure 5:
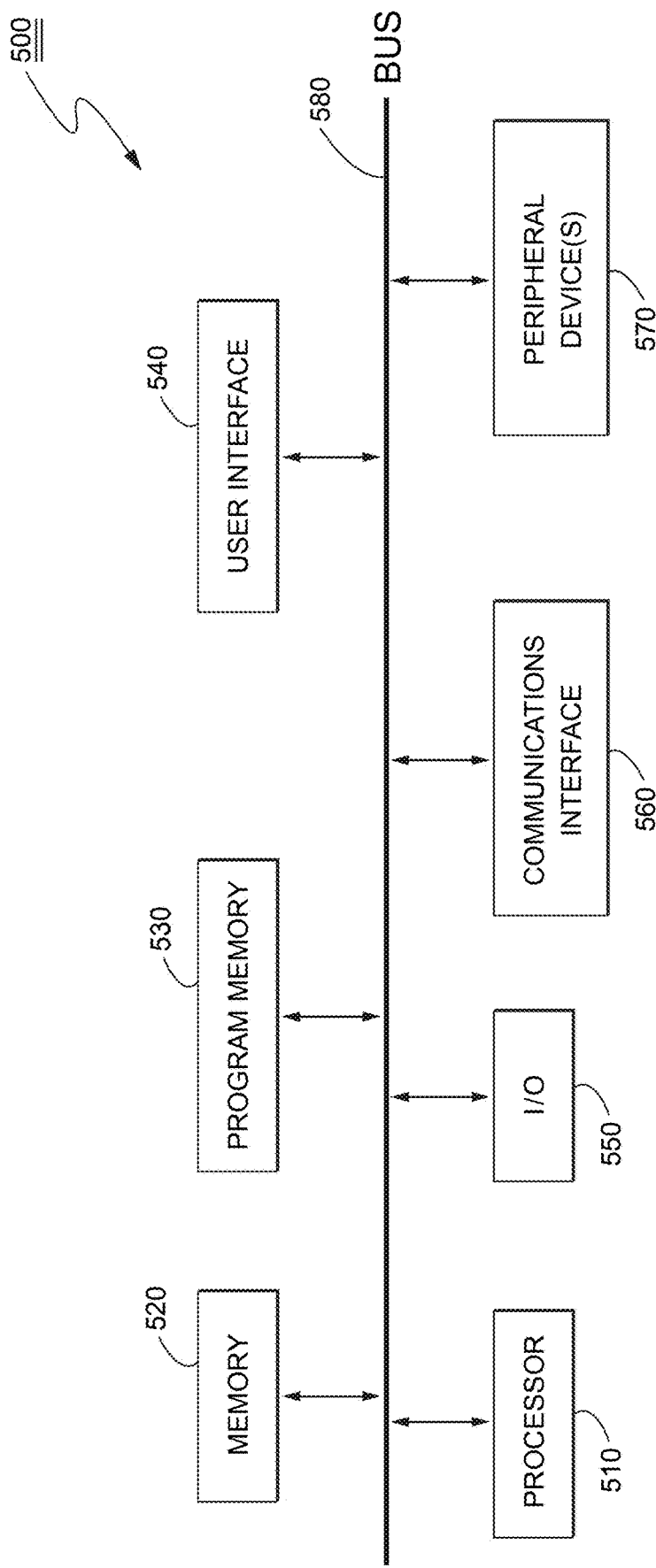
FIG. 5 is an illustrative schematic block diagram of elements of a computing system that may be used to perform functions associated with an example embodiment.

FIG. 5 shows an illustrative schematic block diagram of elements of a computing system that may be used to perform functions associated with an example embodiment, which illustrates the basic requirements of such a computer system

500. In FIG. 5, a bus 580 interconnects a processor 510 with various hardware, firmware and software elements including, for example a memory 520 which may be used to store historical and candidate patient data as well as patient-specific patient-level data generated by the example health care management system described herein. Moreover, it will be understood that this memory is not necessarily integrated with the computing system 500, but may be operatively coupled to the system in any manner, including, for example, via a secured cloud, dedicated links, the Internet, or the like.

The computer system 500 may also include a program memory 530 containing various instructions or application software that may be used to operate the processor 510 and to process data, including, for example, machine-level code to run the basic operations of the processor as well as software for implementing the illustrated health care management system. It will be noted that the program memory 530 may also be integrated in whole or in part with the processor 510 and is not necessarily a separate element as shown in the drawings. The computer system 500 may further include several interfaces that enable various interactions with the system 500. For example, a user interface 540 is provided that allows operators to program the system 500 as well as to enter and manipulate data, and to extract information that may be stored in the memory 520 or other databases connected to the system 500. The user interface 540 may be, for example, in the form of a display and associated input/output devices, such as, for example, a keyboard, mouse, gesture pad, or the like (not shown).

The system 500 may also include a communications interface 560 that provides connections for allowing the system 500 to receive and transmit information to and from external sources via various communications links, including, for example, the Internet, an electronic health records system, dedicated links, secure clouds, or the like. For example, the communications interface 560 may be used to receive historical patient data and candidate patient data or patient-level files generated at another system or site. It is also contemplated that the system 500 may include peripheral devices 570, such as, for example, external memory, a printer, etc. While an example general computing system 500 has been described herein, it will be appreciated that those skilled in the art would be able to devise any suitable computing system to achieve the objects and features described herein with respect to the disclosed example health care management system.

FIGS. 6-12 illustrate example user interfaces for providing information related to the patient medication adherence and provider incentive system as discussed above. FIG. 6 illustrates an example interface providing, at least, a brief summary for the customized bonus incentive for a practitioner having practitioner identification PRID as well as general "welcome" information for introducing the user to the system. As can be seen in FIG. 6, the example interface shows the bonus "progress" for the practitioner PRID for a given quarter. In this example, the practitioner PRID has a bonus payment remaining amount BPR of $2,750.00 with a bonus payment missed amount BPM of $750. The practitioner also has 53 patients needing attention PNA to attend to for purposes of achieving the customized bonus incentive amount. The bonus payment remaining amount BPR may refer to the amount of eligible patients for a practitioner PRID in which bonus payment can be achieved where the bonus payment missed amount BPM may refer to the bonus payment from the number of patients that were not adherent (e.g., did not refill their prescription within an allotted amount of time from their expected prescription refill date, did not receive mammograms within an allotted window of time).

In the example of a BPM for medication adherence, practices may not obtain a bonus if a patient does not fill their prescription within the requisite number of days of the targeted medication as prescribed/indicated by their doctor/practitioner within a defined time interval and/or the practice indicates that the selected patient is not their patient (e.g., the practice notifies of an error in the underlying claims data that caused the system to wrongly attribute a given patient to that practice). The underlying system can accommodate performance measures far beyond adherence, and the specific rules governing the linkage between action/outcome and bonus payment would be customized by the system for each such instance. For example, the system could be configured so that a practice receives a target bonus if the practice successfully converts a patient to a 90-day refill and/or removes the patient from medications deemed to be unsafe as determined by some third-party and recognized clinical standards entity and/or organization. In such examples, the system could be configured to construct a bonus payment reflecting such a setting.

Thus, the system provides a simple and easy to understand metric as to how much compensation a particular practitioner could earn for their patient population as well as how much compensation the practice has missed during a given time period (e.g., quarter). It should be appreciated that the time period of measurement is not limited to a quarter and could be any particular unit of time (e.g., monthly, bi-monthly, yearly).

Figure 7:
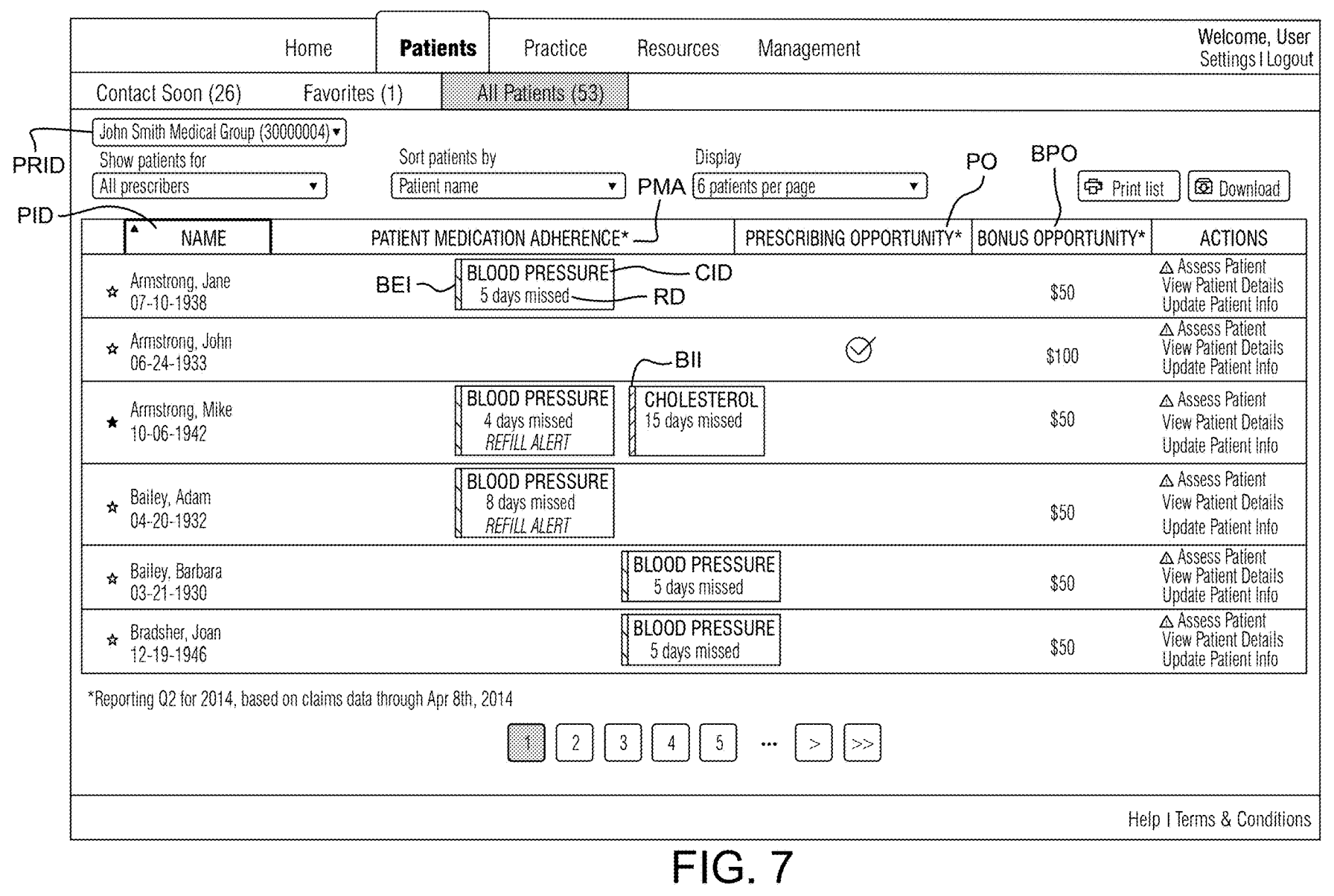

FIG. 7 shows an example interface for displaying a list of patients in the customized incentive program where each patient is shown with their medication adherence PMA, prescribing opportunity PO, and bonus payment opportunity BPO. The interface shows the patients for a particular practitioner PRID where each patient is listed with a patient identification PID (e.g., the patient's first and last name). The patient ID can also include the patient's date of birth as well as any other particular identification information for the patient (e.g., social security number, insurance ID, driver's license number).

As described above, a health care provider (e.g., a health insurance company) could have multiple goals to achieve for its population of patients. These goals could be mandated by, for example, a government agency or could even be goals self-imposed by the organization. These goals could relate to different therapies for each patient. Some of these therapies include, but are not limited to, drug regimens (e.g., blood pressure medications, cholesterol medications, heart medications, etc.) as well as medical services (e.g., mammograms, prostate exams, etc.).

Using the example above, the health care provider may require 75% of its patients be adherent for a particular therapy. If the health care provider only has 71% of its patients being adherent, the protocol 300 may identify a list of patients to make up the remaining 4% by looking at the patient-specific score of patients. Thus, patients having a score within a specified range will be selected in the subset of patients that provide a greater likelihood for the provider to meet its goals. This range can be engineered for each health plan and practice and if the number of patients generated from this list is not big enough, the range can be widened. The resulting list can be shown, for example, in part in FIG. 7 where each patient having patient ID can have a patient-specific score that falls within the "4%" range. It should be appreciated that the list of patients could include more/less patients than the ones required to achieve a particular goal and is not in any way limited to only the patients selected for achieving the goal of a particular program.

In the example shown in FIG. 7, each patient ID is listed in alphabetical order based on the name of the patient. For each patient, the interface can show the patient medication adherence PMA, a prescribing opportunity PO, and/or a bonus payment opportunity for each patient PID. The patient medication adherence PMA shows how adherent a patient is to a drug regimen for treating a particular condition. For example, patient "Jane Armstrong" is shown having a health condition ID CID of "blood pressure" in which the patient is taking a certain drug regimen to treat the blood pressure condition. The interface can show the days past (or days until) the next refill date RD. In this example, 5 days have passed between the current date and the date that "Jane Armstrong" prescription should have been refilled. For example, "Jane Armstrong" may have had a next refill date of May 1, 2014 where the current date could be May 6, 2014.

In this example, even though the patient is 5 days past his/her next refill date, the customized incentive program still leaves the patient listed as being eligible for the bonus payment by a bonus eligible indicator BEI. If the bonus payment is no longer eligible for a given patient and his/her condition, the interface will indicate such by showing a bonus ineligible indicator BII. For example, patient "Mike Armstrong" has missed 15 days since the latest expected prescription refill date RD and thus has not been adherent in refilling the medication to treat the "cholesterol" condition. Thus, "Mike Armstrong" has a bonus ineligible indicator BII representing that the bonus opportunity BPO has been missed for this quarter. It should be understood that the indicators BEI, BII can be represented, for example, using color schemes. For example, indicator BEI could be in the color green indicating that a bonus payment is still possible where indicator BII could be in the color red indicating that a bonus payment opportunity has been missed. Likewise, different color indicators could be used as warning indicators. For example, if the patient is close to being outside of the refill range, the indicator BEI could change from the color green to the color yellow, before changing to indicator BII in color red.

The interface in the example shown in FIG. 7 also shows the bonus payment opportunity BPO for each patient that is adherent to their particular drug regimen. For example, if patient "Jane Armstrong" has been refilling their medication to treat "blood pressure" in a timely manner, the bonus payment opportunity BPO will pay $50 for that particular patient. The display likewise can show multiple therapies where each therapy may have its own bonus payment opportunity. For example, "Mike Armstrong" has blood pressure and cholesterol therapies where each bonus payment opportunity BPO is $50. As the opportunity for cholesterol has been missed in this quarter, the BPO for "Mike Armstrong" is $50 instead of $100.

The display likewise shows a prescribing opportunity PO for each patient. The prescribing opportunity PO could alert the practice if there is an opportunity to add, remove, or change a prescription that, based on other indicators in the patient's medical or pharmacy record, may be appropriate for their care plan. Examples may include a diabetic and hypertensive patient that is not on the evidence-supported ACE/ARB for patients with those two conditions or a patient who is currently over 65 years of age and on a medication considered high-risk for the elderly. It should be appreciated that ACE-ARB can refer to two specific medications used to treat hypertension. These two classes are the angiotensin receptor blockers (ARB drugs) and the angiotensin converting enzyme inhibitors (ACE inhibitors). Both of these classes of drugs lower blood pressure by blocking certain specific steps in the renin-angiotensin-aldosterone (RAA) chain.

Practices can earn a bonus if they address prescribing opportunities flagged in the portal. Prescribing opportunities can be noted with a red flag and, when addressed, can be changed to a green check-mark. It should also be appreciated that the display can be adjusted to show more/less patients as well as more/less health conditions for each patient. The display can also be configured to show multiple bonus payment opportunities BPOs for each payment with different payouts respectively. Of course, the display could be configured to include other various information. For example, the display could also include patients from multiple participating health plans. That is, if a practice serves two or more health plans, the system can be configured to capture both plans as customers of the product, and then the patients selected and displayed for the product could reflect patients from both plans. This could be more advantageous for the practice because the practice will have a single interface to use for viewing patients for both (or all) payers.

Likewise, the display can be adjusted so that the patients are prioritized and/or ordered based on the number of medications/therapies they are engaged. For example, "Mike Armstrong" could be listed at the top as he has multiple therapies (e.g., blood pressure and cholesterol). The system could also eliminate practices that do not have a high enough patient participation number thus making it difficult, if not impossible, for the health care provider to achieve the needed 4% through that particular practice.

Figure 8:
FIG. 8 shows a non-limiting example user interface providing further patient details.

FIG. 8 shows an example interface for providing one or more details for a particular patient PID for a given practitioner PRID. Certain information that can be accessed/displayed in this interface includes, but is not limited to, patient assessment, patient information, additional notes for the patient, and key facts related to the patient. This example interface can also summarize the adherence factors for a particular patient. For example, for patient "Jane Armstrong," the patient medication adherence PMA for "blood pressure" is shown where the patient has missed 5 days since the next expected refill date. This information would likely match the information shown in FIG. 7, but "drilled down" to show more detail for the patient. The medication adherence PMA can also include the specific type of medication MED, the remaining bonus payment opportunity BPO, a refill due date RDD, as well as a prescriber PR. Here, patient "Jane Armstrong" has a 90 day supply of Moexipril-Hydrochlorothiazide for blood pressure to be refilled on Apr. 24, 2014 and prescribed by Dr. Smith. If the patient refills the medication within an allotted window of time before/after the refill due date RDD, a payout of $50 for the patient and/or condition will be rewarded. The refill due date RDD for each patient and their corresponding condition can be recalculated based on when the patient actually refills the prescription (or even based on an estimated refill date) taking into account their supply that was filled. In this example, if "Jane Armstrong" in fact refills the prescription on Apr. 24, 2014, then the next refill due date RDD would be approximately 90 days from Apr. 24, 2014 (i.e., Jul. 23, 2014).

The interface shown in FIG. 8 can also show different factors for assessing a patient PID. For example, a user could select a list of patient assessment features PAF as to why a particular patient has not been consistently adherent to a medication. For example, the patient could have had difficulty reaching the pharmacy and/or the patient did not understand the dosing instructions. It should be appreciated that the list shown in FIG. 8 is only an example and more/less factors can be listed and selected. Likewise, the interface allows for a user to manually enter the particular assessment in a text entry box.

FIG. 9 shows an example interface for showing certain key facts KF1, KF2 for a particular patient. In the example shown in FIG. 9, some key facts KF1, KF2 for this patient include that the patient over the course of the last year has had 5 medications in 5 therapy classes as well as 2 prescribers and 2 pharmacies. The key facts section includes a variable set of facts about the patient based on the medical and pharmacy data accumulated. The key facts portion has options for "displaying always" and "displaying when relevant" which includes different information depending upon the option. This information can be useful in helping to determine why or why not a patient has been adherent to a particular drug regimen. It should be appreciated that the key facts can be derived from data contained within a claims data feed obtained to perform predictions and prioritize patients.

FIG. 10 shows an example interface providing a summary of overall patient adherence as well as the overall bonus payment for a given practitioner PRID. The interface can show a practitioner summary PRS during a given quarter showing, at the least, the type of therapy provided, a number of patients being treated for the therapy, and an average number of untreated days for the type of therapy in the summary PRS. In the example shown in FIG. 10, the practitioner PRID has 19 patients being treated for diabetes where the overall average number of untreated days for the collection of patients is 6.47 days. The display can also list a total number of therapies as well as the average untreated days for all therapies.

In addition to the practitioner summary PRS, the interface can also show a practitioner bonus summary PRBS showing missed and remaining bonus payment amounts for a given period of time. In the example shown in FIG. 10, the practitioner bonus summary extends across a calendar year and shows the missed and remaining bonus payments for a particular quarter (e.g., quarter Q2). Similar to the summary shown in FIG. 6, practitioner PRID has missed $750 in bonus payments where $2,750 in bonus payments are remaining. The summary can also "drill down" to show missed and remaining bonus payments for individual conditions/therapies. It should be appreciated that the summary is not limited to only showing display for a calendar year and can extend for a period of time that is longer or shorter. Likewise, the time period does not necessarily have to be divided into quarters and can be shown as a single period of time or in other different time subdivisions (e.g., monthly). Furthermore, the display could also show the bonus payment amount achieved for a given practitioner during a particular time period.

FIG. 11 shows an example interface providing a practitioner summary level view showing one or more non-participating practices. It should be appreciated that the display could instead show one or more participating practices.

FIG. 11 illustrates a tool for allowing executive users and liaisons of customers to manage and track the progress of practices in the system. Through the tool, they can view the practices onboarding, engagement, and outcome status, as well as key operational information such as the number of users in the practice, their contact information, the number of prescribers in the practice, their contact information, the payment address of the practice, etc.

In the example shown in FIG. 11, each practitioner PRID is listed and given an engagement score ES as to how engaged the practitioner PRID is in helping the patients to become adherent to their respective drug regimens. The summary can also list the specific practitioner name PRNAME, the practitioner region PRREGION, and/or the bonus eligible patients PRBEP for each practitioner. The display can also include other data (e.g., time periods of participation, liaisons) and is not limited to the information described above.

In the example shown in FIG. 11, each practitioner is ranked based on their engagement score ES which is shown, for example, based on a "star" ranking system. For example, a highly engaged practitioner will have four stars, a regularly engaged practitioner will have three stars, a somewhat engaged practitioner will have two stars, and a non-engaged practitioner will have only one star. Practitioners that are not applicable for engagement can be listed with designation "N/A."

The engagement score ES is based on a composite score that may, for example, include, but is not limited to, the following example practice activity metrics: (1) logging into the system on a regular basis (login total adjusted for number of users); (2) user has logged in during the past two weeks; (3) users are accessing their patient list; and/or (4) one or more engaged users (e.g., engaged users login to the system on a regular basis, have on average longer visits and use the system in more detail than other users). The practice can receive "points" for the various activity metrics noted above, which ultimately determines their overall engagement category (e.g., "star" ranking).

Practices are considered highly engaged if they are logging into the system on a regular basis, have logged in during the past two weeks, are accessing their patient list, and have at least one engaged user. These are stand-out practices that are excelling at all of the ways the system measures activity above and beyond how the average 'engaged' practices are performing.

Practices are considered engaged if users login to the system on a regular basis, have on average longer visits and use the system in more detail than other users. Practices are considered somewhat engaged if they are logging into the system and accessing their patient list, but on an irregular basis. Finally, not engaged practices are not logging into the system, have not logged in during the past two weeks, are not accessing their patient list, and do not have any engaged users. The interface in FIG. 11 is useful in that it can show a user how good different practitioners are at making their patients adherent to one or more drug regimens without having to individually examine each practitioner.

Figure 12:
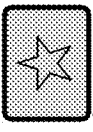
FIG. 12 shows a non-limiting example user interface including practice summary information.

FIG. 12 shows another example interface summarizing practice information for a given practitioner PRID. The display can show the engagement score ES for the practitioner PRID as well as the number of bonus eligible patients PRBEP for a given practitioner PRID. Among other pieces of information, the interface can also show the list of providers PRL for each practitioner PRID where contact information is provided for the respective provider PRL as well as the number of members attended to by the provider PRL. The interface can also be configured to provide an engagement score for each individual provider PRL to determine which specific providers are more or less engaged than others.

It should be appreciated that the above-describe techniques are not limited to applying the incentive to each patient and could be applied to, for example, a group of patients. As an example, a scenario could exist where a practice has 10 patients to manage and the system does not apply a per-patient bonus. Instead, the system could provide an overall performance bonus. For example, if at an end of a quarter all 10 patients are adherent, the practice could receive a total of $1,000; if 9 are adherent, the practice receives $900; if 8 are adherent, the practice receives $800; and if 7 are adherent, the practice receives $700. If the practice has less than 7 that are adherent, the system may not award the practice any bonus (i.e., $0). Likewise, the practice could receive the entire bonus amount of a minimum threshold in the pool of patients is satisfied (e.g., if the practice has at least 7 patients being adherent they receive the full $1,000).

Such a configuration is advantageous in situations where the expected number of patients that are adherent without intervention is at a minimum amount. Using the example above, this configuration would be beneficial in situations where 6 of the 10 patients at the practice would be adherent without any intervention. Thus, under this configuration the practice will receive no credit unless they surpass their expected adherence rate. Such a configuration could eliminate "dead-weight" losses of the program and actually allow larger bonuses for those remaining (e.g., if the system channels all the bonus paid to the patient who would already have been adherent to the bonus amount if their panel rate of adherence exceeds an expected value). Thus, such a configuration advantageously prevents practices from participating in the program without actually performing no intervention (and still getting paid the bonus amount).

As discussed above, the technology described in this application is directed to an iterative data process comprising a) prediction, b) patient selection/prioritization, c) and evaluation analytics to continuously optimize performance on medication quality indicators at a population level, including medication adherence. This technology uses patients' predicted future medication outcomes, other patient characteristics derived from patient data, and intervention capacity attributes to compute the most cost-effective intervention recommendation for each individual patient on a recurring basis based on accumulating data.

The technology aims to achieve increased patient adherence to selected medication regimens and improvements in other quality and efficiency measures in defined patient populations. For example, this technology is equally effective in other medical services (which could include services related to both adherence as well as non-adherence), including, but not limited to, mammogram services, prostate exams, services for patients at risk of opioid (e.g., pain medication) overutilization, services for patients taking two more drugs that conflict with each other and should not be taken together, services for patients on excessive amounts of "high risk medications," services for patients at risk of not taking certain medications as directed (e.g., patients with behavioral health diagnoses who are at risk of not taking prescribed medications), and/or other behavioral health issues including depression, attention deficit disorder (ADHD), and/or bipolar disorder. The system is also effective for specialty medications that payers could be concerned about from a cost and/or utilization perspective including, but not limited to, drugs to treat Hepatitis C, MS, Crohn's, and others.

The system described herein is also effective for other various medical services including services related to reducing hospital readmissions. For example, the system could target incentives on behalf of members who are predicated to have a strong likelihood of being readmitted. Likewise, this system could also be employed in a pharmacy/pharmaceutical setting. In such a scenario, the incentive plan may not necessarily apply (e.g., the plan may not be responsible for providing incentives) and/or the user interface could be configured so that it is made available to pharmacy staff (e.g., instead of staff for a health care provider).

The technical field is health care and health care data analytics. The technology helps facilitate efficient population-level improvements in medication adherence and other health care outcomes. The technology leverages the use of patient-level predictions about future health care outcomes to inform the design and delivery of patient engagement activities.

The technology establishes the basis for innovative, prediction-driven performance improvement programs in health care that have the potential to improve the prevalence and performance of health care financial bonus programs for health care professionals designed to achieve targeted improvements in health care outcomes, including medication adherence commensurate with the value that those very targeted improvements create to sponsors of such programs. The technology constitutes the core enabler of new products that support health care improvement programs using financial incentives to encourage new and/or better informed actions by health care professionals to engage patients in new ways, including taking their medications consistently as prescribed.

In the above-description, for purposes of explanation and non-limitation, specific details are set forth, such as particular nodes, functional entities, techniques, protocols, standards, etc. in order to provide an understanding of the described technology. It will be apparent to one skilled in the art that other embodiments may be practiced apart from the specific details described below. In other instances, detailed descriptions of well-known methods, devices, techniques, etc. are omitted so as not to obscure the description with unnecessary detail. Individual function blocks are shown in the figures. Those skilled in the art will appreciate that the functions of those blocks may be implemented using individual hardware circuits, using software programs and data in conjunction with a suitably programmed microprocessor or general purpose computer, using applications specific integrated circuitry (ASIC), and/or using one or more digital signal processors (DSPs). The software program instructions and data may be stored on computer-readable storage medium and when the instructions are executed by a computer or other suitable processor control, the computer or processor performs the functions. Although databases may be depicted as tables below, other formats (including relational databases, object-based models, and/or distributed databases) may be used to store and manipulate data.

Although process steps, algorithms or the like may be described or claimed in a particular sequential order, such processes may be configured to work in different orders. In other words, any sequence or order of steps that may be explicitly described or claimed does not necessarily indicate a requirement that the steps be performed in that order. The steps of processes described herein may be performed in any order possible. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the technology, and does not imply that the illustrated process is preferred.

Various forms of computer readable media/transmissions may be involved in carrying data (e.g., sequences of instructions) to a processor. For example, data may be (i) delivered from RAM to a processor; (ii) carried over any type of transmission medium (e.g., wire, wireless, optical, etc.); (iii) formatted and/or transmitted according to numerous formats, standards or protocols, such as Ethernet (or IEEE 802.3), SAP, ATP, Bluetooth, and TCP/IP, TDMA, CDMA, 3G, etc.; and/or (iv) encrypted to ensure privacy or prevent fraud in any of a variety of ways well known in the art.

While the technology has been described in connection with what is presently considered to be an illustrative practical and preferred embodiment, it is to be understood that the technology is not to be limited to the disclosed embodiment, but on the contrary, is intended to cover various modifications and equivalent arrangements.

The invention claimed is:

1. A system configured to identify a patient population in a healthcare program based on, in part, a predictive function applied to characteristics of a patient, the system comprising:
   a processor; and
   a memory configured to store computer readable instructions that, when executed by the processor, cause the system to:
      determine a list of health care providers and a list of patients;
      obtain one or more data files including historical data for each patient;
      apply the historical data to one or more variables and generate a resultant data file;
      apply the resultant data file to a model setup procedure to generate a prediction function;
      generate an adherence risk score for each patient, in the list of patients, using the prediction function;
      apply the score to each patient in the list of patients;
      identify a subset of patients, from the listing of patients, based on, at least, factors related to a likelihood of adherence after an intervention is carried out; and
      generate a user interface for display having at least a first view, a second view, and a third view, wherein the first view includes:
         a home menu display having a plurality of selectable options; and
      the second view includes:
         an itemized listing of patients from the subset of patients, wherein each line in the itemized listing includes an identification of each patient and at least one therapy associated with each patient, and each patient in the itemized listing is associated with the applied score; and
      the third view includes patient details associated with a first patient from the itemized listing of patients, and the third view further includes:
         a first portion identifying a therapy associated with the first patient, and an indication associated with a refill value for the therapy associated with the first patient.

2. The system of claim 1, wherein the home menu display includes a text portion having introductory text.

3. The system of claim 1, wherein
   a first option, from the plurality of selectable options, includes a patient list option, and
   selection of the patient list option enables changing of display from the first view to the second view.

4. The system of claim 1, wherein the third view includes a financial indicator in association with the first patient and the associated therapy.

5. The system of claim 1, wherein the third view includes a first portion having barrier assessment indicators for identifying one or more barriers associated with adherence to the therapy associated with the first patient.

6. The system of claim 1, wherein the third view includes indication of bonus opportunity associated with the therapy.

7. The system of claim 1, wherein the third view includes indication of a prescriber associated with the therapy.

8. The system of claim 1, wherein generating the adherence risk score for each patient comprises:
   defining relevant time periods for analyzing the historical data;
   defining a dependent variable indicative of a measure to be predicted;
   determining at least one independent predictor variable;
   creating the resultant data file including the dependent and independent variable; and
   deriving the adherence risk score based on the resultant data file.

9. The system of claim 1, wherein the model setup procedure includes dividing the resultant data file into a training data file and a validation data file.

10. A method for identifying a patient population in a healthcare program, the method comprising:
    at an information processing system including at least one processor:
       determining a list of health care providers and a list of patients;
       obtaining one or more data files including historical data for each patient;
       applying the historical data to one or more variables and generate a resultant data file;
       applying the resultant data file to a model setup procedure to generate a prediction function;
       generating an adherence risk score for each patient, in the list of patients, using the prediction function;
       applying the score to each patient in the list of patients;
       identifying a subset of patients, from the listing of patients, based on, at least, factors related to a likelihood of adherence after a given intervention is carried out; and
       generating a user interface for display having at least a first view, a second view, and a third view, wherein the first view includes:
          a home menu display having a plurality of selectable options; and
       the second view includes:
          an itemized listing of patients from the subset of patients, wherein each line in the itemized listing includes an identification of each patient and at least one therapy associated with each patient, and each patient in the itemized listing is associated with the applied score; and
       the third view includes patient details associated with a first patient from the itemized listing of patients, and the third view further includes:
    a first portion identifying a therapy associated with the first patient, and an indication associated with a refill value for the therapy associated with the first patient.

11. The method of claim 10, wherein the user interface further includes indication of adherence opportunity associated with a practice group.

12. The method of claim 10, wherein the user interface further includes an identification of a number of patients associated with a practice group.

13. The method of claim 10, wherein the user interface further includes a bar graph reflecting an adherence opportunity associated with a practice group.

14. The method of claim 10, wherein the user interface further includes a first portion identifying adherence opportunities achieved by a practice group, and a second portion identifying adherence opportunities currently unachieved by the practice group.

15. A non-transitory computer readable storage medium storing computer readable instructions that, when executed by a processor, cause the processor to provide execution comprising:
   determining a list of health care providers and a list of patients;
   obtaining one or more data files including historical data for each patient;
   applying the historical data to one or more variables and generate a resultant data file;
   applying the resultant data file to a model setup procedure to generate a prediction function;
   generating an adherence risk score for each patient, in the list of patients, using the prediction function;
   applying the score to each patient in the list of patients;
   identifying a subset of patients, from the listing of patients, based on, at least, factors related to a likelihood of adherence after an intervention is carried out; and
   generating a user interface for display having at least a first view, a second view, and a third view, wherein the first view includes:
      a home menu display having a plurality of selectable options; and
   the second view includes:
      an itemized listing of patients from the subset of patients, wherein each line in the itemized listing includes an identification of each patient and at least one therapy associated with each patient, and each patient in the itemized listing is associated with the applied score; and
   the third view includes patient details associated with a first patient from the itemized listing of patients, and the third view further includes:
      a first portion identifying a therapy associated with the first patient, and an indication associated with a refill value for the therapy associated with the first patient.

16. The non-transitory computer readable storage medium of claim 15, wherein the user interface further includes an indication associated with practice group participation.

17. The non-transitory computer readable storage medium of claim 15, wherein the user interface further includes numerical values associated with adherence opportunities of patients within each practice group from a plurality of practice groups.

18. The non-transitory computer readable storage medium of claim 15, wherein the user interface further includes information details associated with a first practice group from a plurality of practice groups.

19. The non-transitory computer readable storage medium of claim 18, wherein selection of an item in the second view enables changing of display from the second view to the third view.

20. The non-transitory computer readable storage medium of claim 18, wherein the user interface further includes an identification of prescribing opportunity associated with at least the first practice group from the plurality of practice groups.

* * * * *